United States Patent
Duschka

[11] Patent Number: 5,923,721
[45] Date of Patent: Jul. 13, 1999

[54] BI-PLANE X-RAY DIAGNOSTIC APPARATUS

[75] Inventor: Hartmut Duschka, Uttenreuth, Germany

[73] Assignee: Siemens Aktiengesellschaft, Munich, Germany

[21] Appl. No.: 08/906,428

[22] Filed: Aug. 5, 1997

[30] Foreign Application Priority Data

Aug. 19, 1996 [DE] Germany .......... 196 33 359.8

[51] Int. Cl.$^6$ .......... H05G 1/70

[52] U.S. Cl. .......... 378/92; 378/101

[58] Field of Search .......... 378/92, 101

[56] References Cited

U.S. PATENT DOCUMENTS 3,999,044 12/1976 Grim .......... 378/92
4,349,740 9/1982 Grassmann et al. .......... 378/92

*Primary Examiner*—Craig E. Church

[57] ABSTRACT

A bi-plane x-ray diagnostic apparatus has two x-ray tubes and two radiation receivers for respectively obtaining images from an examination subject in two different planes. Both x-ray tubes are fed by a single high-frequency generator, having a common chain therein including an intermediate DC voltage circuit, an inverse rectifier and a high-voltage transformer. Emission of x-rays from each of the x-ray tubes ensues via pulses supplied to control grids in the respective x-ray tubes. The operating parameters and the dose can be independently set for the respective images in the two planes.

1 Claim, 2 Drawing Sheets

BI-PLANE X-RAY DIAGNOSTIC APPARATUS

BACKGROUND OF THE INVENTION

1. Field of the Invention

The present invention is directed to a bi-plane x-ray diagnostic installation, suitable for undertaking medical examinations.

2. Description of the Prior Art

The use of a bi-plane x-ray diagnostic apparatus having two x-ray sources and a radiation receiver, for example an x-ray image intensifier, seated at a C-arm, are for cardiological examinations is described in U.S. Pat. No. 5,515,416. As a result of this construction, the patient can be transirradiated from two different directions. Known bi-plane x-ray diagnostic systems employ two independent, separate x-ray generators for respectively feeding the two x-radiators.

German OS 25 23 886 discloses an x-ray diagnostic apparatus having two x-ray tubes activatable in alternation and a common high-voltage generator, the high-voltage generator being operated with the line frequency. Switching between the x-ray tubes ensues with electronic switch mechanisms that precede the x-ray tubes. No details regarding the setting of the x-ray tube voltage and the x-ray tube current are disclosed. German OS 29 08 767 discloses a high-frequency x-ray diagnostic generator with an inverter preceded by an intermediate DC voltage circuit, wherein the setting of the high-voltage at the following x-ray tube ensues via the inverter and the intermediate DC voltage circuit.

Nothing regarding simplification of the structure of a bi-plane x-ray diagnostic apparatus is discussed in this document.

German OS 20 31 595 discloses an x-ray stereo arrangement with grid-controlled x-ray tubes. Details with respect to the setting the x-ray tube voltage, the x-ray tube current and of the dose are not recited.

SUMMARY OF THE INVENTION

An object of the present invention is to provide a bi-plane x-ray diagnostic apparatus of the type described above which is simpler in view of the feed of the x-ray sources and less expensive compared to known bi-plane systems.

This object is inventively achieved in a bi-plane x-ray diagnostic apparatus having, a high-frequency x-ray generator formed by a single chain composed of an intermediate DC voltage circuit, an inverter and a high-voltage transformer for both x-ray sources. The activation of the x-ray emission ensues by grid pulses for the two x-ray sources. The operating data for the two x-ray sources (KV, MA) can be independently set for both planes. The exposure or fluoroscopy dose for the two planes is correspondingly set by pulses.

DESCRIPTION OF THE PREFERRED EMBODIMENTS

Figure 1:
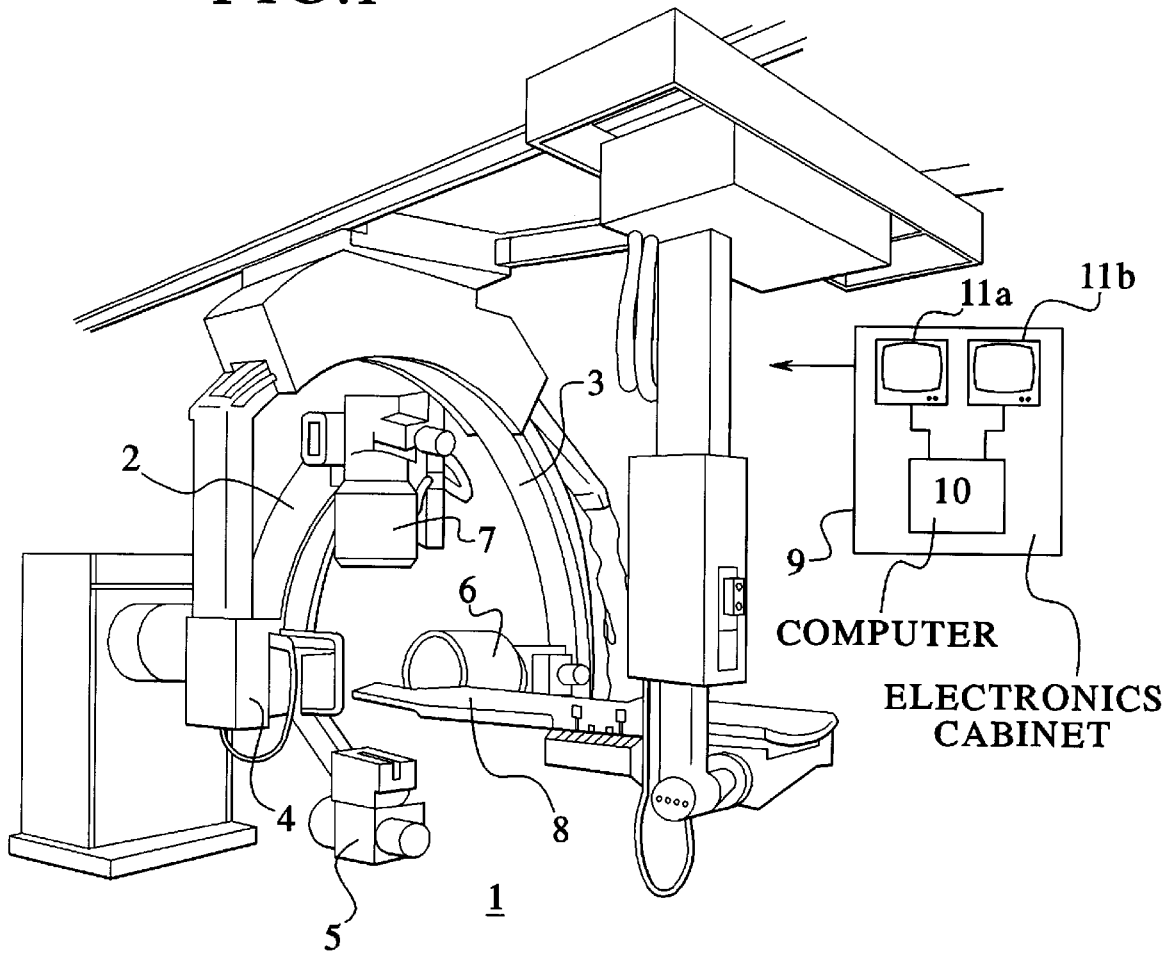
FIG. 1 shows a bi-level x-ray diagnostic apparatus according to the invention.

FIG. 1 shows a bi-plane x-ray diagnostic apparatus 1 for angiography having two C-bends 2 and 3 that respectively carry x-ray sources 4 and 5 and x-ray image intensifiers 6 and 7 at their ends. The x-ray source 4 and the x-ray image intensifier 6, and the x-ray source 5 and the x-ray image intensifier 7 are respectively aligned to one another. The central rays of the two x-ray sources 4 and 5 are offset by 90° relative to one another in one plane. It is thereby possible to transirradiate a patient lying on a table 8 from two directions perpendicular to one another and, accordingly, to produce two x-ray survey exposures from these directions. The angle between the two central rays need not necessarily amount to 90°, but can have a value deviating therefrom.

The x-ray diagnostic apparatus 1 has an electronics cabinet 9 that feeds and controls the exposure units 4, 6 and 5, 7 and receives the image data of the x-ray image intensifiers 6 and 7 that are registered with the assistance of video cameras, and processes these data with a computer 10 into images that can be reproduced on monitors 11a and 11b. The overview exposures produced from different directions thus can be reproduced on the monitors 11a and 11b.

In particular, the x-ray diagnostic apparatus 1 makes it possible to generate empty and filled images of blood vessels on the basis of a suitable injection of contrast agent into the body of the patient. Digital subtraction angiography images being generated from these empty and filled images with the computer 10.

Figure 2:
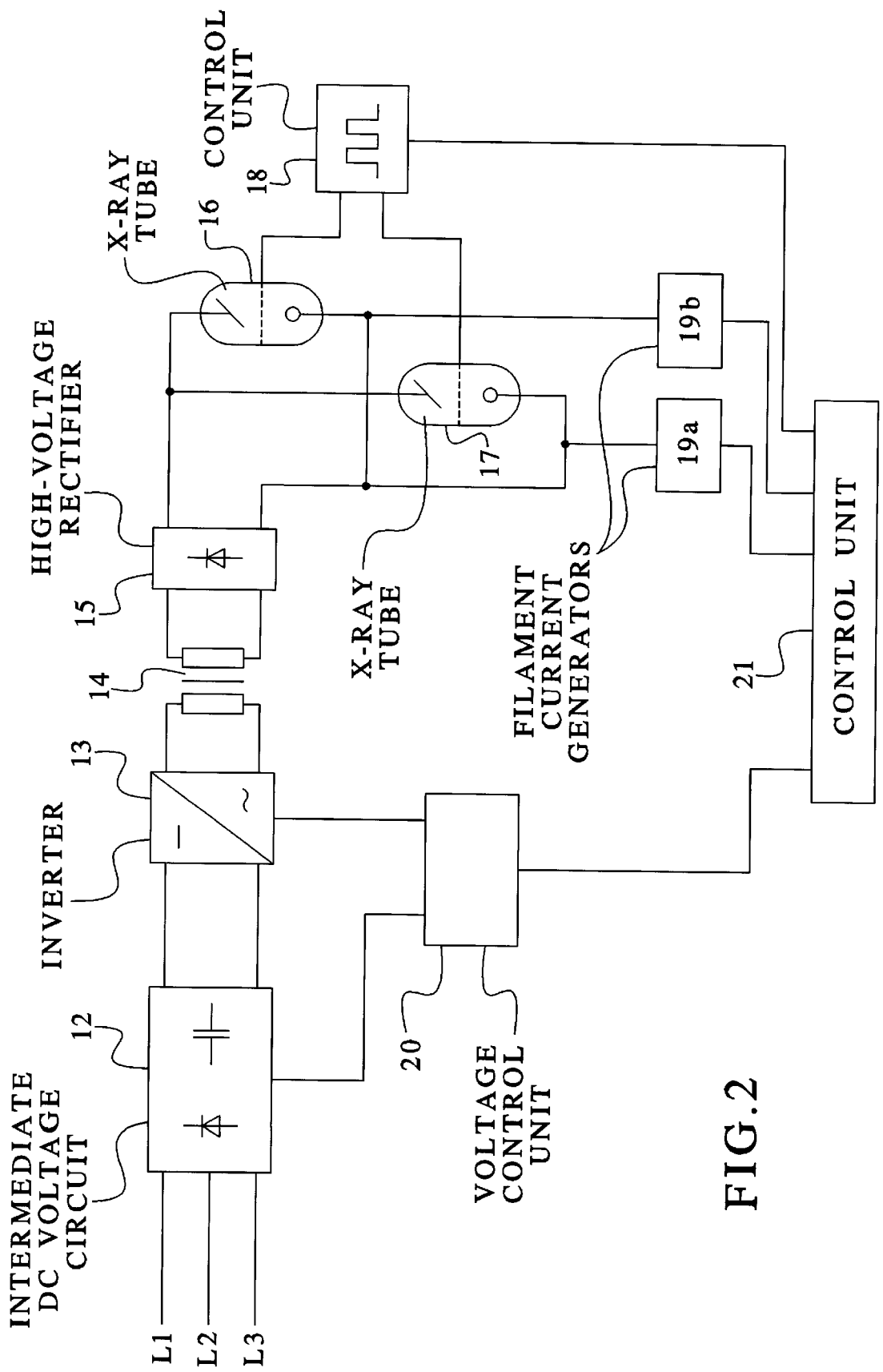
FIG. 2 is a block diagram of the x-ray generator of the x-ray diagnostic apparatus of FIG. 1.

FIG. 2 shows an inventive x-ray generator which would be arranged in the electronics cabinet 9 for feeding the x-ray sources 4 and 5 in detail. An intermediate DC voltage circuit 12 is connected to the alternating current network (mains), the output voltage thereof being supplied to an inverter 13 that feeds a high-voltage transformer 14. A high-voltage rectifier 15 is connected to the output of the high-voltage transformer 14 and the x-ray tubes 16 and 17 of the two x-ray sources 4 and 5 are connected to the output of this high-voltage rectifier 15. The x-ray tubes 16 and 17 are grid-controlled. A control unit 18 is allocated to them. Separate filament current generators 19a and 19b via which the x-ray tube currents can be individually set for the tubes 16 and 17 are provided for generating the tube current for the x-ray tubes 16 and 17. A voltage control unit 20 is provided for setting the x-ray tube voltage. The coordination and synchronization of the control ensues with a higher-ranking, shared control unit 21.

The alternating activation of the x-radiation of the two x-ray tubes 16 and 17 ensues with the control unit 18 that supplies control pulses to the control grids of the x-ray tubes 16 and 17 in alternation. The control unit 21 enables the independent setting of the operating data (x-ray tube voltage, x-ray tube current) for the two x-ray tubes 16 and 17. Accordingly, the exposure or fluoroscopic dose for the two levels is independently set by the pulses of the control unit 18.

Although modifications and changes may be suggested by those skilled in the art, it is the intention of the inventor to embody within the patent warranted hereon all changes and modifications as reasonably and properly come within the scope of his contribution to the art.

I claim as my invention:

1. A bi-plane x-ray diagnostic apparatus comprising:
   a first x-ray tube and a first radiation receiver disposed for receiving radiation from said first x-ray tube;
   a second x-ray tube and a second radiation receiver disposed for receiving radiation from said second x-ray tube;
   means for mounting said first x-ray tube and said first radiation receiver and said second x-ray tube and said second radiation receiver relative to each other for obtaining respective images of an examination subject in two different planes;

a high-frequency generator connected to each of said first and second x-ray tubes for supplying power to each of said first and second x-ray tubes, said high-frequency x-ray generator comprising a common chain therein, connected to each of said first and second x-ray tubes, including an intermediate DC voltage circuit, an inverse rectifier and a high-voltage generator;

each of first and second x-ray tubes having a control grid therein and means for controlling emission of said x-rays respectively from said first and second x-ray tubes by pulses supplied to the respective control grids;

a first filament current generator for supplying a first filament current to said first x-ray tube and a second filament current generator for supplying a second filament current to said second x-ray tube; and control means for operating said first and second x-ray tubes in alternation, said control means being connected to said intermediate voltage circuit, said inverter, said first filament current generator and said second filament current generator, and said control means comprising means for operating said intermediate voltage circuit and said inverter and said first current generator during operation of said first x-ray tube to set a voltage and said first filament current for said first x-ray tube, and for operating said intermediate voltage circuit and said inverter and said second filament current generator during operation of said second x-ray tube to set a voltage and said second filament current for said second x-ray tube, said voltage and said second filament current for said second x-ray tube being independent of said voltage and said first filament current for said first x-ray tube.

* * * * *